US008081262B1

(12) United States Patent
Perez (10) Patent No.: US 8,081,262 B1
(45) Date of Patent: Dec. 20, 2011

(54) SAFETY SUN GLASSES WITH HIGH INTENSITY LIGHT PROTECTION

(76) Inventor: Jose R. Perez, Manahawkin, NJ (US)

( * ) Notice: Subject to any disclaimer, the term of this patent is extended or adjusted under 35 U.S.C. 154(b) by 1274 days.

(21) Appl. No.: 11/789,253

(22) Filed: Apr. 24, 2007

(51) Int. Cl.
*G02F 1/1335* (2006.01)
*G02F 1/1333* (2006.01)

(52) U.S. Cl. .............. 349/14; 349/13; 349/58; 2/8.1; 2/8.2

(58) Field of Classification Search .............. None
See application file for complete search history.

(56) References Cited

U.S. PATENT DOCUMENTS

| | | | |
|---|---|---|---|
| 4,868,930 A | 9/1989 | Blackstone | |
| 5,276,539 A * | 1/1994 | Humphrey | 349/14 |
| 5,343,258 A | 8/1994 | Lachman et al. | |
| 5,671,035 A * | 9/1997 | Barnes | 351/45 |
| D394,732 S | 5/1998 | Huh | |
| 5,790,230 A | 8/1998 | Sved | |
| D401,608 S | 11/1998 | Eberle et al. | |
| 5,959,705 A * | 9/1999 | Fergason | 349/14 |
| D431,328 S | 9/2000 | Tanner | |
| 6,185,739 B1 | 2/2001 | Verkic et al. | |
| 6,401,244 B1 | 6/2002 | Kramer et al. | |
| 7,008,055 B2 * | 3/2006 | McLear et al. | 351/44 |
| 7,753,518 B2 * | 7/2010 | Lam et al. | 351/41 |

* cited by examiner

*Primary Examiner* — Tina Wong
(74) *Attorney, Agent, or Firm* — Montgomery Patent & Design, LLC; Robert C. Montgomery; Joseph T. Yaksich (57) ABSTRACT

A pair of safety sunglass, particularly for use when arc welding, includes auto darkening lenses having suitable characteristics for providing high intensity light protection during welding procedures. The sunglasses have a tight fitting frame conforming to an individual's face curvature. When an arc is struck, or another high intensity light source is present, the lenses instantly and automatically darken to protect the individual's eyes from damage. Each lens includes a plurality of layers for prohibiting the high intensity direct light rays from passing therethrough. A feature and benefit of such eyewear is that welding operations may be performed in confined spaces where a conventional welding face shield can not fit. When the welding is completed, the eyeglasses would quickly return to their sun tinted state allowing them to be used as a conventional pair of sunglasses.

15 Claims, 4 Drawing Sheets

SAFETY SUN GLASSES WITH HIGH INTENSITY LIGHT PROTECTION

RELATED APPLICATIONS

The present invention was first described in Disclosure Document No. 590,456 filed on Nov. 22, 2005.

FIELD OF THE INVENTION

This invention relates to welding sunglasses and, more particularly, to welding sunglass form-fitted for use in space-confined areas. The sunglasses include means for automatically darkening the lenses when a predetermined quantity of high intensity direct light rays are detected by a photoelectric sensor such that a user can be safely shielded from undesirable welding arcs and light respectively.

BACKGROUND OF THE INVENTION

Arc welding is a process that is used in a multitude of industries and hobbies. Due to the nature of the arc, vast amounts of ultraviolet (UV) radiation are released which poses a severe danger to one's eyesight. To help combat this radiation, welding masks which use a very high level of tinted glass, are flipped down over the user's eyes right before the arc is struck. While the arc is moving, adequate illumination is provided to illuminate the work pieces. While such a method does work, it is sometimes cumbersome to use. Also, there are times when someone may be welding in a confined space, which may not allow the welding helmet to be used. To help in these situations, some people resort to using sunglasses. This however does not provided adequate protection, as the lenses are not dark enough. Even if lenses of an adequate tint were used, there is no way to flip them down at the last instance as the arc is struck. Accordingly, a need exists for a means by adequate eye protection for arc welding can be provided without the shortcomings and disadvantages as listed above. The development of the present invention fulfills this need.

Several attempts have been made in the past to develop a welding helmet employing a photochromic lens that automatically changes color based upon detected ambient light. U.S. Pat. No. 6,401,244 in the name of Kramer, et al discloses a welding helmet comprising: a face portion defined by a wall about the perimeter of the face portion, extending toward the interior of the welding helmet; a flange extending from the interior end of the wall; a sloped outer portion about the exterior perimeter of the face portion; and at least one opening in the flange adjacent a first portion of the wall, the at least one opening having a protrusion therein protruding parallel to the flange. The welding helmet may also comprise a plurality of channels in a second portion of the wall. The welding helmet may also include a face plate for covering the face portion of the welding helmet comprising a bezel and an interior groove about the perimeter of the bezel. Unfortunately, this prior art example does not provide a means for detecting high intensity direct light rays wherein a tint level of the lenses are automatically adjusted to protect user eyes.

U.S. Pat. No. 6,185,739 in the name of Verkic, et al discloses a light shielding helmet system that includes a helmet shell configured for placement on the head of a user and at least two interchangeable lens holders having different lens-holding configurations. Each lens holder holds one or more lens plates and each can be releasably mounted on the helmet shell. The lens holders can be of different styles (e.g., flip up or fixed front) and/or hold lens plates of different sizes. Unfortunately, this prior art example also does not provide a means of for detecting high intensity direct light rays wherein a tint level of the lenses are automatically adjusted to protect user eyes.

U.S. Pat. No. 5,959,705 in the name of Fergason describes a switch activating system for an automatically darkening lens system and an automatically darkening lens system including such a switch activating system, includes a cover plate through at least part of which a scene may be viewed, a support, a pair of switch electrodes, one switch electrode positioned in relatively fixed relation with said support, the other switch electrode being positioned for movement with respect to said one switch electrode selectively to make electrical connection therewith in response to deflecting of said cover plate. The automatically darkening lens assembly also includes a controllable light shutter for controlling transmission of light for viewing therethrough, and a circuit for operating said light shutter and affecting operating characteristics thereof. A method for operating an auto-darkening welding lens including an operating circuit includes selecting an operational characteristic of the welding lens by setting a characteristic of the circuit, said setting comprising deflecting a mechanical member of the welding lens to operate a switch. Unfortunately, this example is complicated to use and includes a variety of circuits which may become damaged or inoperable over extended usage, thus rendering the invention cumbersome for its intended purpose.

U.S. Pat. No. 4,868,930 in the name of Blackstone discloses protective eye wear useful as sunglasses, safety glasses, or the like. The product includes a unitary plastic lens piece or shield having a uniform thickness. The side edges of the lens piece are folded rearwardly to form side shields. A brow member is attached to the top edge of the lens piece and extends along the entire length of the lens piece and is perpendicular to the lens piece. Temple members can be attached to the ends of the lens piece or shield. The eye wear product can be made from plastic sheets. Unfortunately, this example is not suitable for use as protective eyewear during welding operations and the like because of its size.

None of the prior art particularly describes a pair of tight fitting glasses with auto darkening lenses for use during welding operations. Accordingly, there is a need for a protective ocular shield for use in confined spaces when performing welding operations. The use of the present invention provides personal protective equipment for a user's eyes in a manner which still allows welding in a tight confined space.

SUMMARY OF THE INVENTION

In view of the foregoing disadvantages inherent in the prior art, it has been observed that there is a need a welding helmet employing a photochromic lens that automatically changes color based upon detected ambient light.

The apparatus includes a curvilinear frame partially fitted around a head of a user such that eyes of the user are covered. A pair of coextensively shaped lenses is directly attached to the frame, without the use of intervening elements, and disposed at a front area of the frame. Each of such lenses conveniently includes a plurality of laminated and contiguously abutted layers covering an entire surface area of each of the lenses respectively.

The apparatus further includes a mechanism for automatically darkening a tint of the lenses when high intensity direct light rays are detected above a predetermined threshold level during the welding operations. Such an automatic darkening mechanism includes a photoelectric light sensor centrally located on the frame and forwardly facing away from the frame, which is essential such that the high intensity direct light rays traveling towards the lenses also advantageously strike the photoelectric light sensor and are effectively detected by the photoelectric light sensor. A battery compartment is monolithically formed within the frame and positioned rearward of the lenses. Such a battery compartment is provided with an associated cover removably engaged therewith.

The automatic darkening mechanism further includes a power supply source removably nested within the battery compartment, and a power switch located forward of the battery compartment. Such a power switch is electrically mated to the power supply source and is advantageously adaptable between three distinct positions effectively defined as an off position, an on-inactive position and an on-active position respectively. The lenses are partially tinted, which is critical for allowing the user to view surrounding objects under normal ambient light conditions when the switch is toggled to the off position as well as the on-inactive position. The lenses are fully tinted, which is crucial for advantageously restricting a maximum quantity of the high intensity direct light rays when the switch is adapted to the on-active position.

The automatic darkening mechanism further includes a driver circuit electrically coupled to the switch and the photoelectric light sensor respectively. Such a photoelectric light sensor effectively generates and transmits an input signal to the driver circuit based upon a quantity of the high intensity light rays detected during welding operations. Such a driver circuit effectively generates and transmits output signals to the first and second liquid crystal apertures respectively, which is critical for regulating passage of the high intensity direct light arrays through the lenses during the on and off positions respectively.

The frame includes first and second ear support members, and a bridge member medially positioned between the first and second ear support members and monolithically formed therewith. Such a bridge member is registered perpendicular to the first and second ear support members. Such first and second ear support members are oppositely disposed on left and right sides of the frame. The first and second ear support members are aligned parallel to each other, which is vital for maintaining a static spatial relationship therebetween during operating and non-operating conditions.

Each of the lenses includes a plurality of discrete layers assembled in a laminated format. Such discrete layers include a first and outer most layer defining a replaceable protective plate which is detachable from remaining ones of the discrete layers after extended use, a second layer including an ultraviolet light and infrared light filter directly coupled to the first layer, without the use of intervening elements, which is essential for continuously blocking harmful ultraviolet and infrared light rays while the switch is toggled to the on and off positions respectively, a third layer defining a first polarizing lens, which is critical for restricting high intensity direct light rays which are polarized in a predetermined orientation, and a fourth layer defining a first liquid crystal aperture, which is crucial for filtering out the polarized high intensity direct light rays that pass through the first polarizing lens.

Each of the lenses further includes a fifth layer defining a second polarizing lens directly coupled to the fourth layer, without he use of intervening elements, a sixth layer defining a second liquid crystal aperture cooperating with the fifth layer and directly coupled thereto, without the use of intervening elements, a seventh layer defining a third polarizing lens, which is vital for providing an additional filter stage and thereby blocking all of the high intensity light rays generated during welding operations, an eighth layer directly coupled to the seventh layer, without the use of intervening elements, and defining an intermediate protective layer, which is essential for sealing and protecting the first, second, third, fourth, fifth, sixth and seventh layers from undesirable foreign debris, and an inner most located ninth layer removably attached to the eight layer for defining a replaceable protective film.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY

| | |
|---|---|
| 10 | sport-type protective welding glasses for confined space utilization |
| 15 | user |
| 20 | frame system |
| 25 | extraneous light rays |
| 30 | auto darkening lens |
| 35 | photoelectric light sensor |
| 37 | direct light rays |
| 40 | battery compartment cover |
| 45 | side ear piece |
| 50 | batteries |
| 55 | battery compartment |
| 60 | power switch |
| 65 | logo areas |
| 70 | first ear support member |
| 75 | frame bridge piece |
| 80 | second ear side support member |
| 85 | outer replaceable protective plate |
| 90 | ultraviolet and infrared filter |
| 95 | first polarizing lens |
| 100 | first liquid crystal aperture |
| 105 | second polarizing lens |
| 110 | second liquid crystal aperture |
| 115 | third polarizing lens |
| 120 | intermediate protective cover |
| 125 | inner replaceable protective plate |
| 130 | display driver circuit |

DETAILED DESCRIPTION OF THE PREFERRED EMBODIMENT

The best mode for carrying out the invention is presented in terms of its preferred embodiment, herein depicted within FIGS. 1 through 4. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

Figure 1:
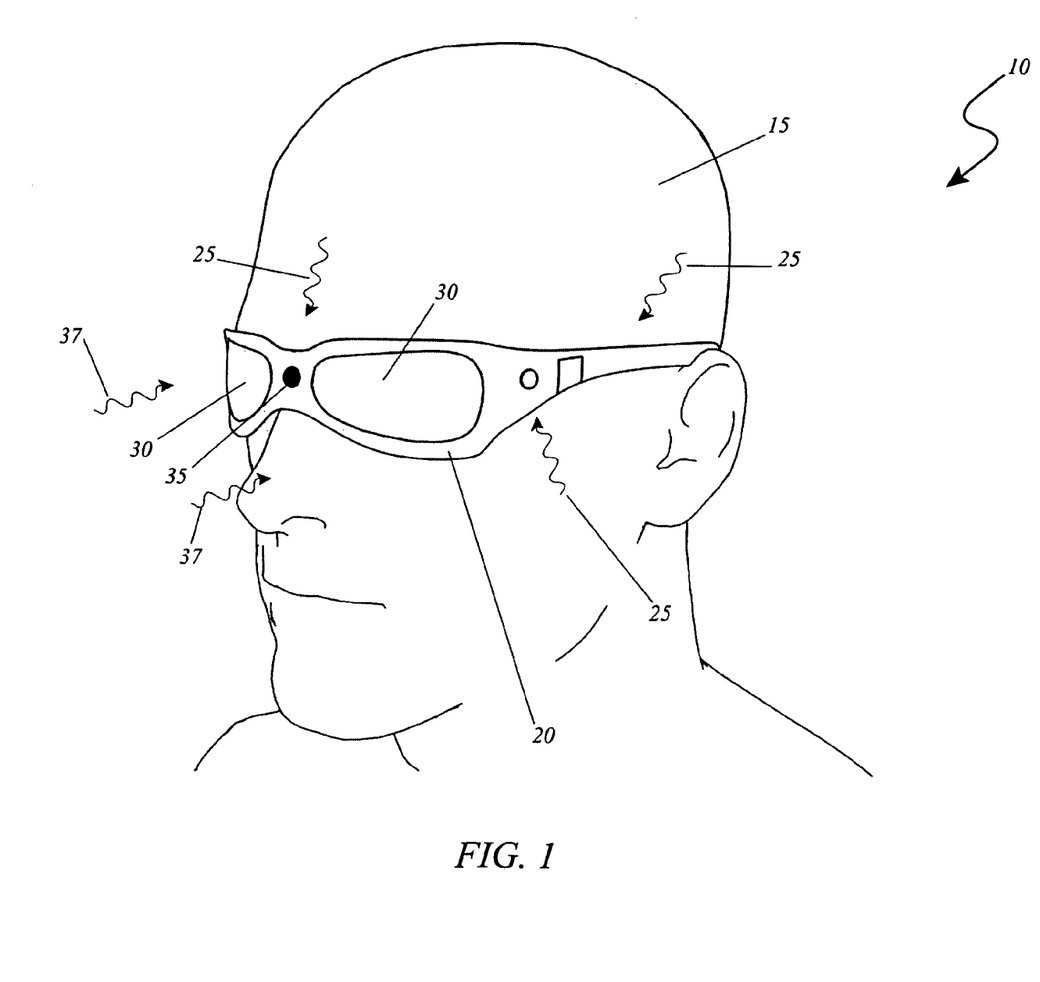
FIG. 1 is an isometric view of the sport type protective welding glasses for confined space utilization 10 shown in an utilized state on a user 15, according to the preferred embodiment of the present invention.

Referring to FIG. 1, an isometric view of the sport-type protective welding glasses for confined space utilization 10 shown in a utilized state on a user 15, according to the preferred embodiment of the present invention is disclosed. The user 15 wears the sport type protective welding glasses for confined space utilization 10 on his or her face such that it covers the eye area. A frame system 20 comprises the overall outer housing of the sport-type protective welding glasses for confined space utilization 10 and provides several essential functions. First, it provides an overall look that is aesthetically pleasing and provides an active, sport look that is generally appealing to all types of user 15. Such attractiveness is envisioned to generally encourage use. Secondly, the frame system 20 provides a fit that is generally close to the eye area of the user 15. The frame system 20 is designed to be curvilinear to effectively fit around the head of the user 15 such that the eyes of the user 15 are covered.

A series of extraneous light rays 25 are generally unable to access the eye area of the user 15, thus providing increased eye and light protection for the user 15. Finally, the close fitting nature of the frame system 20 reduces the possibility that the frame system 20 will become caught or snagged on nearby objects when the user 15 is welding in close or confined quarters. An auto darkening lens 30 is provided within the front area of the frame system 20, as would be customarily expected. Said auto darkening lens 30 allows the user to view outward. The auto darkening lens 30 uses known technology currently used in full face welding helmets. The auto darkening lens 30 will be described in greater detail herein below. A photoelectric light sensor 35 is centrally located on the frame system 20 as part of the auto darkening feature of the auto darkening lens 30. The forward facing nature of the photoelectric light sensor 35 ensures that direct light rays 37 that will strike the auto darkening lens 30 will also strike the photoelectric light sensor 35 thus enabling operation as will be described in greater detail herein below.

Figure 2:
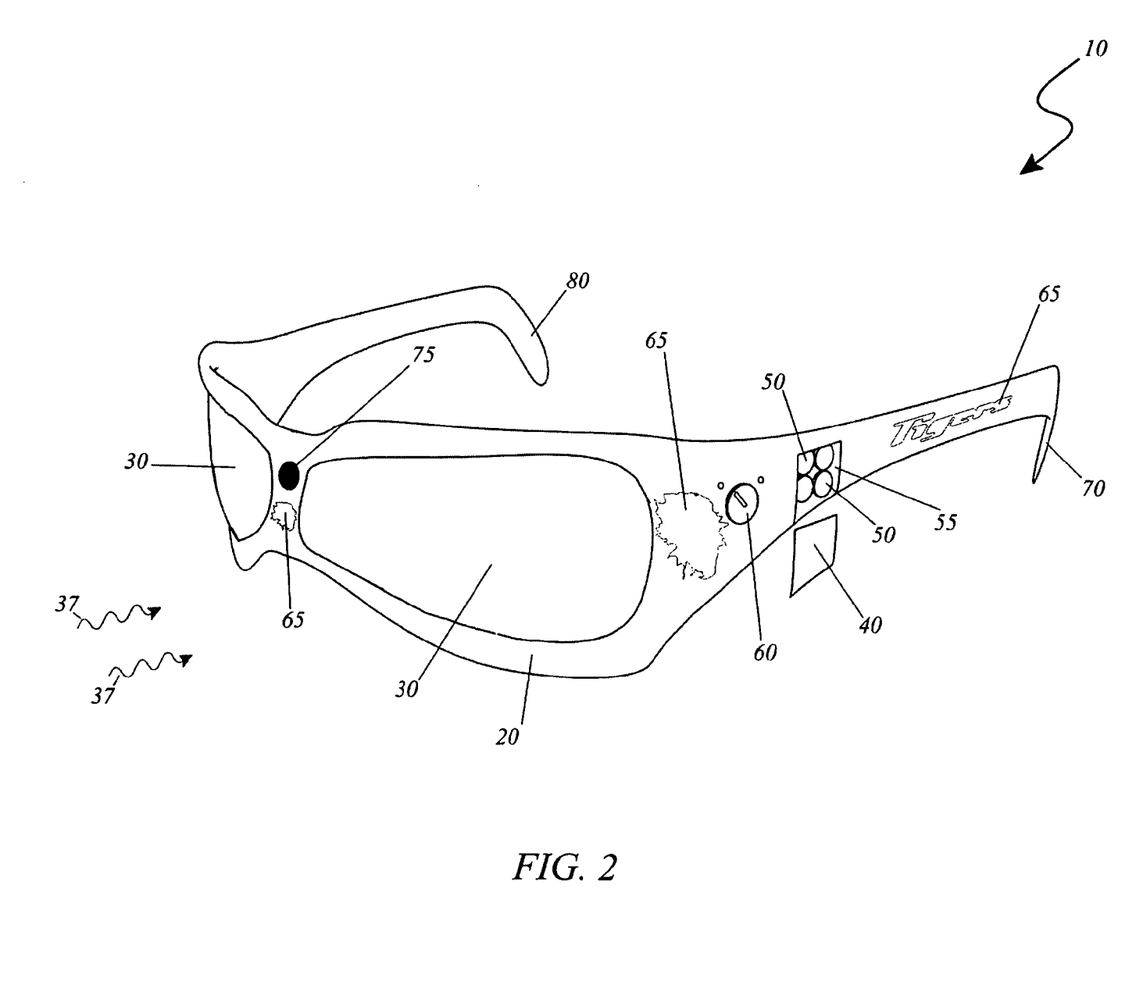
FIG. 2 is a detailed isometric view of the sport type protective welding glasses for confined space utilization 10.

Referring now to FIG. 2, a detailed isometric view of the sport-type protective welding glasses for confined space utilization 10 is depicted. A battery compartment cover 40 is shown in a removed state from a side ear piece 45. A series of batteries 50 which power the sport type protective welding glasses for confined space utilization 10 are visible in a battery compartment 55. The batteries 50 are envisioned to be of the small watch type variety to allow for use in the lightweight configuration of the frame system 20 such as, but not limited to, lithium button cells, silver oxide, manganese alkaline button cells, or other batteries.

A power switch 60 is located immediately forward of the battery compartment 55 to allow for ease of activation in a one handed operation. In it's OFF position, the auto darkening lenses 30 are of a slightly tinted nature that allows viewing under normal ambient light conditions. In its ON but inactive position, the auto darkening lens 30 are of the same slightly tinted nature that allows for viewing through the auto darkening lens 30 under normal ambient light conditions. In its ON and active position, the auto darkening lens 30 are severely tinted so as to restrict the transference of the direct light rays 37 through the auto darkening lens 30. Such darkening is associated with protection against high intensity light generally associated with welding protection. Those skilled in the art will realize that the protection against high intensity light is only afforded to the eye area of the user 15 (as shown in FIG. 1), and other areas of the face are left unprotected.

However, it should be noted that use of the sport type protective welding glasses for confined space utilization 10 is intended for those areas which are confined and unable to accommodate a full face shield as would typically be worn. It should be generally agreed that the protection against direct light rays 37 of a high intensity nature as provided by the sport type protective welding glasses for confined space utilization 10 would be more appropriate than no protection at all.

A series of logo areas 65 are located about the frame system 20 as shown. Said logo areas 65 can be used for the display of a variety of aesthetically pleasing motifs and/or other images such as, but not limited to, cartoon characters, sport logos, flames, and/or other motif designs. Other themes for the logo areas 65 envisioned include, but are not limited to, country flags, state flags, animals, characters, and/or the addition of inscriptions such as the user's name, special dates, quotes, and/or other terms and expressions instead of or in combination with the motifs.

The frame system 20 comprises a first ear support member 70 attaching to one side of a frame bridge piece 75, extending in a perpendicular manner as expected with conventional eyewear. In addition, a second ear side support member 80 attaches to the opposite side of the frame bridge piece 75 in a perpendicular manner to the frame bridge piece 75 and parallel to the first ear support member 70. Due to internal electrical components as described above and to be described herein below, the first ear support member 70 and the second ear side support member 80 are not capable of retracting inwardly with respect the to the frame bridge piece 75, a feature typically found in common eyeglasses and sunglasses.

Figure 3:
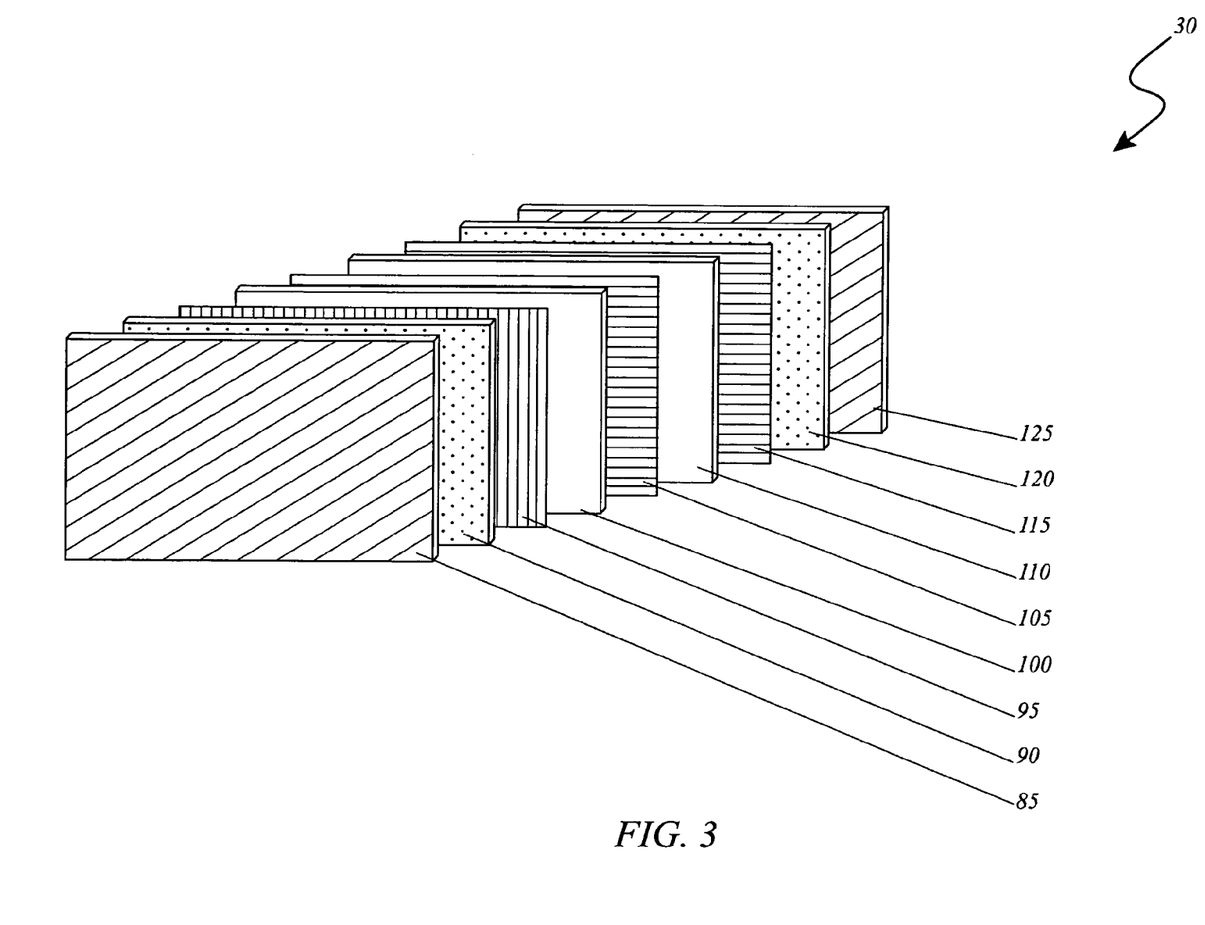
FIG. 3 is an exploded cross sectional view of the auto darkening lens 30 as used with the sport type protective welding glasses for confined space utilization 10; and, FIG. 4 is an electrical schematic diagram depicting the major components of the sport type protective welding glasses for confined space utilization 10.

Referring next to FIG. 3, an exploded cross sectional view of the auto darkening lens 30 as used with the sport type protective welding glasses for confined space utilization 10 is shown. The auto darkening lens 30 consists of nine (9) discrete layers assembled in a laminated format. The most outward of these is an outer replaceable protective plate 85 which can be replaced should it become scratched, pitted or otherwise unsuitable for use.

The next is an ultraviolet and infrared filter 90, which continually blocks harmful radiation, whether the auto darkening lens 30 is ON, OFF, activated or deactivated. Next in progression is a first polarizing lens 95 that restricts direct light rays 37 (as shown in FIG. 1) by only allowing said rays to pass, which are aligned or polarized in a predetermined orientation. Following the first polarizing lens 95 is a first liquid crystal aperture 100 which functions as a shutter to filter out direct light rays 37 (as shown in FIG. 1) that are let through by the first polarizing lens 95. Said first liquid crystal aperture 100 is similar in nature to those found on LCD displays, such as on watches, cameras, and the like.

Next in sequence is a second polarizing lens 105 which works in conjunction with a second liquid crystal aperture 110 and a third polarizing lens 115 to provide additional filter stages and effectively block all direct light rays 37 (as seen in FIG. 1) that are of a high intensity nature such as provided by a welding arc. Following said layers, an intermediate protective cover 120 is provided which effectively seals and protects the laminated layers aforementioned described. Finally, a inner replaceable protective plate 125 is provided, which similarly to the outer replaceable protective plate 85, can be replaced by the user 15 (as shown in FIG. 1) should it become scratched, permanently soiled or otherwise unusable.

Figure 4:
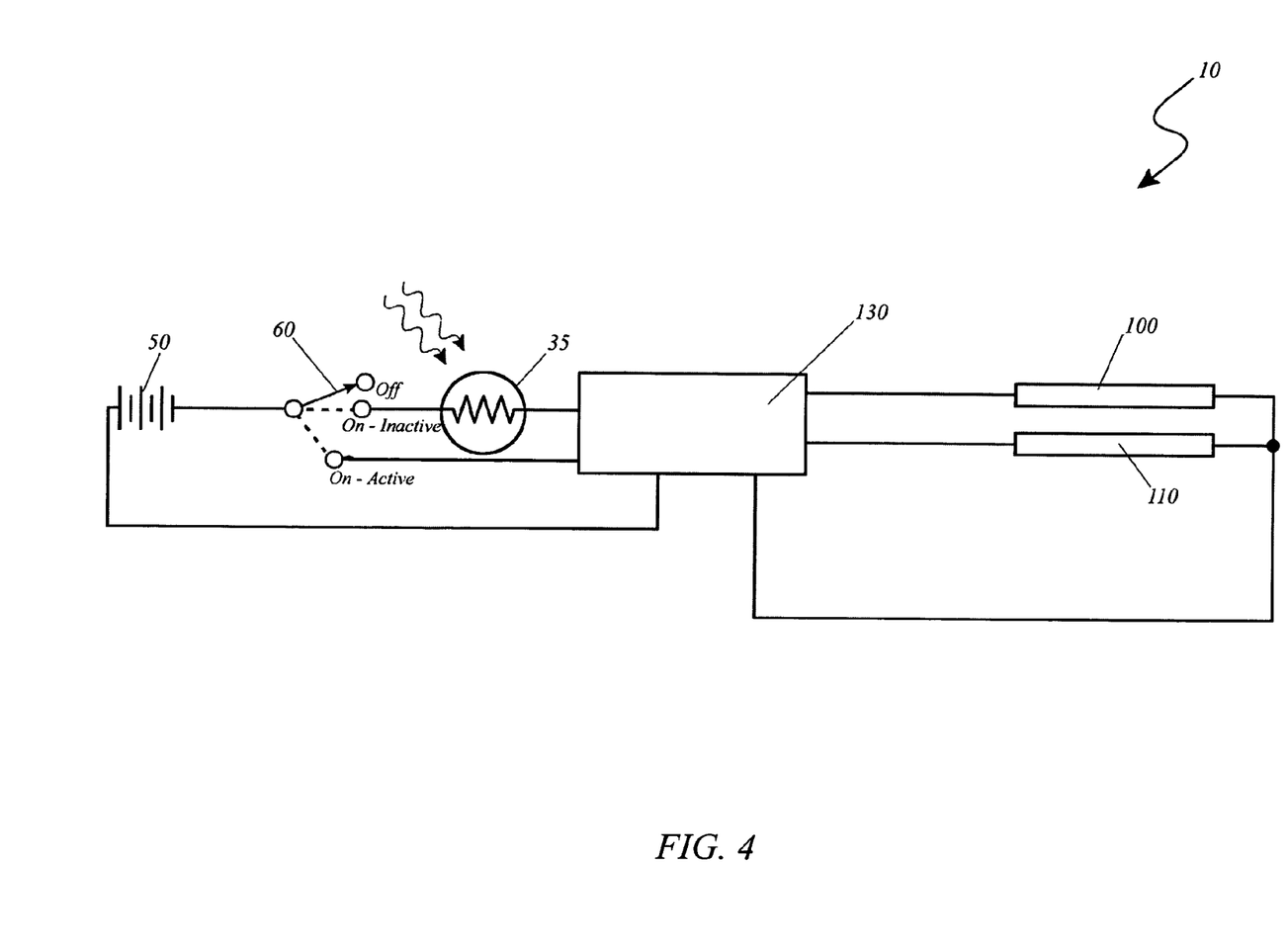

Referring finally to FIG. 4, an electrical schematic diagram depicting the major components of the sport-type protective welding glasses for confined space utilization 10 is disclosed. Power from the batteries 50 is routed through the power switch 60 that serves as the only single user control of the sport type protective welding glasses for confined space utilization 10. The resultant power is routed to a display driver circuit 130. Such driver circuits are well known by those skilled in the art. The photoelectric light sensor 35 serves to provide an input signal to the display driver circuit 130 that allows it to function in the manner aforementioned described. An output is generated to drive the first liquid crystal aperture 100 and the second liquid crystal aperture 110 to their desired state whether inactive or active. It should be noted that should the direct light rays 37 (as shown in FIG. 1) be blocked in way from reaching the photoelectric light sensor 35 that said photoelectric light sensor 35 will not function. Such unwanted blockages may occur from hats, hair, nearby objects and the like which may be present in confined spaces.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After purchase of the sport type protective welding glasses for confined space utilization 10, the user would place the batteries 50 into the battery compartment 55 and replace the battery compartment cover 40. At this point the sport-type protective welding glasses for confined space utilization 10 is ready for operation.

At the beginning of an operation in a confined space which may expose the user 15 to direct light rays 37 of a high intensity nature, the user 15 would activate the sport-type protective welding glasses for confined space utilization 10 by placing the power switch 60 in its ON position, and place the sport-type protective welding glasses for confined space utilization 10 upon their face in the same manner as conventional eyewear. When the arc or other high intensity light source is generated, the direct light rays 37 will strike the photoelectric light sensor 35 and cause the display driver circuit 130 to drive or activate the first liquid crystal aperture 100 and the second liquid crystal aperture 110 to their active state in a manner of milliseconds.

In such a state, the eyes of the user 15 are protected from intense UV radiation and subsequent damage. At the completion of said operation, the direct light rays 37 will direct the display driver circuit 130 to drive the first liquid crystal aperture 100 and the second liquid crystal aperture 110 back to their passive or inactive state. In such a state or an OFF state as directed by the power switch 60, the user 15 may wear the sport-type protective welding glasses for confined space utilization 10 as a conventional pair of tinted eyewear or sunglasses. At the completion of use, the user 15 would place the power switch 60 in its OFF position and store the sport type protective welding glasses for confined space utilization 10 away until needed again.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A protective ocular shield for use in confined spaces when performing welding operations, said ocular shield comprising:
    a curvilinear frame partially fitted around a head of a user such that eyes of the user are covered:
    a pair of lenses directly attached to said frame and disposed at a front area of said frame, each of said lenses comprising a plurality of laminated and contiguously abutted layers covering an entire surface area of each of said lenses, respectively, such that said lenses automatically darken when high intensity light direct rays are detected above a predetermined threshold level;
    a photoelectric light sensor centrally located on said frame and forwardly facing away from said frame such that said high intensity direct light rays traveling towards said lenses also strike said photoelectric light sensor and are detected by said photoelectric light sensor;
    a battery compartment monolithically formed within said frame and positioned rearward of said lenses, said battery compartment being provided with an associated cover removably engaged therewith;
    a power supply source removably nested within said battery compartment; and,
    a power switch located forward of said battery compartment, said power switch being electrically mated to said power supply source and being adaptable between three distinct positions defined as an off position, an on-inactive position and an on-active position respectively;
    wherein said lenses are partially tinted for allowing the user to view surrounding objects under normal ambient light conditions when said switch is toggled to said off position and to said on-inactive position;
    wherein said lenses are fully tinted for restricting a maximum quantity of said high intensity direct light rays when said switch is toggled to said on-inactive position and in response to said high intensity light rays being detected by said photoelectric light sensor, and,
    wherein said lenses are fully tinted for restricting a maximum quantity of said high intensity direct light rays when said switch is toggled to said on-active position.

2. The ocular shield of claim 1, wherein said frame comprises:
    first and second ear support members; and,
    a bridge member medially positioned between said first and second ear support members and monolithically formed therewith, said bridge member being registered perpendicular to said first and second ear support members;
    said first and second ear support members being oppositely disposed on left and right sides of said frame, said first and second ear support members being aligned parallel to each other and maintaining a static spatial relationship therebetween during operating and non-operating conditions.

3. The ocular shield of claim 1, wherein each of said lenses comprises:

a plurality of discrete layers assembled in a laminated format, wherein said discrete layers include;
a first and outer most layer defining a replaceable protective plate which is detachable from remaining ones of said discrete layers after extended use;
a second layer including an ultraviolet light and infrared light filter directly coupled to said first layer for continuously blocking harmful ultraviolet and infrared light rays while said switch is toggled to the on and off positions respectively;
a third layer defining a first polarizing lens for restricting high intensity direct light rays which are polarized in a predetermined orientation; and,
a fourth layer defining a first liquid crystal aperture for filtering out the polarized high intensity direct light rays that pass through said first polarizing lens.

4. The ocular shield of claim 3, wherein each of said lenses further comprises:
a fifth layer defining a second polarizing lens directly coupled to said fourth layer;
a sixth layer defining a second liquid crystal aperture cooperating with said fifth layer and directly coupled thereto;
a seventh layer defining a third polarizing lens for providing an additional filter stage and thereby blocking all of the high intensity light rays generated during welding operations;
an eighth layer directly coupled to said seventh layer and defining an intermediate protective layer for sealing and protecting said first, second, third, fourth, fifth, sixth and seventh layers from undesirable foreign debris; and,
an inner most located ninth layer removably attached to said eight layer for defining a replaceable protective film.

5. The ocular shield of claim 1, further comprising:
a driver circuit electrically coupled to said switch and said photoelectric light sensor respectively, said photoelectric light sensor generating and transmitting an input signal to said driver circuit based upon a quantity of the high intensity light rays detected during welding operations, said driver circuit generating and transmitting output signals to said first and second liquid crystal apertures respectively for regulating passage of the high intensity direct light arrays through said lenses during the on and off positions respectively.

6. A protective ocular shield for use in confined spaces when performing welding operations, said ocular shield comprising:
a curvilinear frame partially fitted around a head of a user such that eyes of the user are covered:
a pair of coextensively shaped lenses directly attached to said frame and disposed at a front area of said frame, each of said lenses comprising a plurality of laminated and contiguously abutted layers covering an entire surface area of each of said lenses respectively, such that said lenses automatically darken when high intensity light direct rays are detected above a predetermined threshold level;
a photoelectric light sensor centrally located on said frame and forwardly facing away from said frame such that said high intensity direct light rays traveling towards said lenses also strike said photoelectric light sensor and are detected by said photoelectric light sensor;
a battery compartment monolithically formed within said frame and positioned rearward of said lenses, said battery compartment being provided with an associated cover removably engaged therewith;
a power supply source removably nested within said battery compartment; and,
a power switch located forward of said battery compartment, said power switch being electrically mated to said power supply source and being adaptable between three distinct positions defined as an off position, an on-inactive position and an on-active position respectively;
wherein said lenses are partially tinted for allowing the user to view surrounding objects under normal ambient light conditions when said switch is toggled to the off position and to said on-inactive position;
wherein said lenses are fully tinted for restricting a maximum quantity of said high intensity direct light rays when said switch is toggled to said on-inactive position and in response to said high intensity light rays being detected by said photoelectric light sensor, and,
wherein said lenses are fully tinted for restricting a maximum quantity of the high intensity direct light rays when said switch is toggled to said on-active position.

7. The ocular shield of claim 6, wherein said frame comprises:
first and second ear support members; and,
a bridge member medially positioned between said first and second ear support members and monolithically formed therewith, said bridge member being registered perpendicular to said first and second ear support members;
said first and second ear support members being oppositely disposed on left and right sides of said frame, said first and second ear support members being aligned parallel to each other and maintaining a static spatial relationship therebetween during operating and non-operating conditions.

8. The ocular shield of claim 7, wherein each of said lenses comprises:
a plurality of discrete layers assembled in a laminated format, wherein said discrete layers include;
a first and outer most layer defining a replaceable protective plate which is detachable from remaining ones of said discrete layers after extended use;
a second layer including an ultraviolet light and infrared light filter directly coupled to said first layer for continuously blocking harmful ultraviolet and infrared light rays while said switch is toggled to the on and off positions respectively;
a third layer defining a first polarizing lens for restricting high intensity direct light rays which are polarized in a predetermined orientation; and,
a fourth layer defining a first liquid crystal aperture for filtering out the polarized high intensity direct light rays that pass through said first polarizing lens.

9. The ocular shield of claim 8, wherein each of said lenses further comprises:
a fifth layer defining a second polarizing lens directly coupled to said fourth layer;
a sixth layer defining a second liquid crystal aperture cooperating with said fifth layer and directly coupled thereto;
a seventh layer defining a third polarizing lens for providing an additional filter stage and thereby blocking all of the high intensity light rays generated during welding operations;
an eighth layer directly coupled to said seventh layer and defining an intermediate protective layer for sealing and protecting said first, second, third, fourth, fifth, sixth and seventh layers from undesirable foreign debris; and, an inner most located ninth layer removably attached to said eight layer for defining a replaceable protective film.

10. The ocular shield of claim 6, further comprising:

a driver circuit electrically coupled to said switch and said photoelectric light sensor respectively, said photoelectric light sensor generating and transmitting an input signal to said driver circuit based upon a quantity of the high intensity light rays detected during welding operations, said driver circuit generating and transmitting output signals to said first and second liquid crystal apertures respectively for regulating passage of the high intensity direct light arrays through said lenses during the on and off positions respectively.

11. A method for automatically darkening a plurality of sunglass lenses for shielding user eyes during high intensity welding operations executed in spaced-confined locations, said method comprising the steps of:

a. providing a curvilinear frame partially fitted around a head of a user such that eyes of the user are covered;

b. providing a pair of lenses directly attached to said frame and disposed at a front area of said frame, each of said lenses comprising a plurality of laminated and contiguously abutted layers covering an entire surface area of each of said lenses respectively, wherein said lenses are coextensively shaped; and, c. providing means for automatically darkening a tint of said lenses when high intensity direct light array are detected above a predetermined threshold level during the welding operations, wherein step c. further comprises the steps of:

i. providing a photoelectric light sensor centrally located on said frame and forwardly facing away from said frame such that the high intensity direct light rays traveling towards said lenses also strike said photoelectric light sensor and are detected by said photoelectric light sensor;

ii. providing a battery compartment monolithically formed within said frame and positioned rearward of said lenses, said battery compartment being provided with an associated cover removably engaged therewith;

iii. providing a power supply source removably nested within said battery compartment; and, iv. providing a power switch located forward of said battery compartment, said power switch being electrically mated to said power supply source and being adaptable between three distinct positions defined as an off position, an on-inactive position and an on-active position respectively;

wherein said lenses are partially tinted for allowing the user to view surrounding objects under normal ambient light conditions when said switch is toggled to the off position as well as the on-inactive position; and wherein said lenses are fully tinted for restricting a maximum quantity of the high intensity direct light rays when said switch is adapted to the on-active position.

12. The method of claim 11, wherein step a. further comprises the steps of i. providing first and second ear support members; and, ii. providing a bridge member medially positioned between said first and second ear support members and monolithically formed therewith, said bridge member being registered perpendicular to said first and second ear support members;

said first and second ear support members being oppositely disposed on left and right sides of said frame, said first and second ear support members being aligned parallel to each other and maintaining a static spatial relationship therebetween during operating and non-operating conditions.

13. The method of claim 11, wherein step b. further comprises the steps of:

i. providing a plurality of discrete layers assembled in a laminated format, wherein said discrete layers include;

ii. providing a first and outer most layer defining a replaceable protective plate which is detachable from remaining ones of said discrete layers after extended use;

iii. providing a second layer including an ultraviolet light and infrared light filter directly coupled to said first layer for continuously blocking harmful ultraviolet and infrared light rays while said switch is toggled to the on and off positions respectively;

iv. providing a third layer defining a first polarizing lens for restricting high intensity direct light rays which are polarized in a predetermined orientation; and, v. providing a fourth layer defining a first liquid crystal aperture for filtering out the polarized high intensity direct light rays that pass through said first polarizing lens.

14. The method of claim 13, wherein step b. further comprises the steps of:

i. providing a fifth layer defining a second polarizing lens directly coupled to said fourth layer;

ii. providing a sixth layer defining a second liquid crystal aperture cooperating with said fifth layer and directly coupled thereto;

iii. providing a seventh layer defining a third polarizing lens for providing an additional filter stage and thereby blocking all of the high intensity light rays generated during welding operations;

iv. providing an eighth layer directly coupled to said seventh layer and defining an intermediate protective layer for sealing and protecting said first, second, third, fourth, fifth, sixth and seventh layers from undesirable foreign debris; and, v. providing an inner most located ninth layer removably attached to said eight layer for defining a replaceable protective film.

15. The method of claim 11, wherein step c. further comprises the steps of:

i. providing a driver circuit electrically coupled to said switch and said photoelectric light sensor respectively, said photoelectric light sensor generating and transmitting an input signal to said driver circuit based upon a quantity of the high intensity light rays detected during welding operations, said driver circuit generating and transmitting output signals to said first and second liquid crystal apertures respectively for regulating passage of the high intensity direct light arrays through said lenses during the on and off positions respectively.

* * * * *